US012697098B2

(12) United States Patent
Shi et al.

(10) Patent No.: US 12,697,098 B2
(45) Date of Patent: Aug. 4, 2026

(54) METHODS AND SYSTEMS FOR AUTOMATED CENTER POSITIONING FOR RADIAL VELOCITY MAPPING IN VECTOR CONTRAST IMAGING

(71) Applicant: KONINKLIJKE PHILIPS N.V., Eindhoven (NL)

(72) Inventors: William Tao Shi, Wakefield, MA (US); Shiying Wang, Melrose, MA (US); Claudia Errico, Medford, MA (US); Mingxin Zheng, Cambridge, MA (US); Thanasis Loupas, Kirkland, WA (US); Paul Sheeran, Woodinville, WA (US); Charles Tremblay-Darveau, Seattle, WA (US); Jeffry Earl Powers, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 18/698,907

(22) PCT Filed: Oct. 10, 2022

(86) PCT No.: PCT/EP2022/078016
§ 371 (c)(1),
(2) Date: Apr. 5, 2024

(87) PCT Pub. No.: WO2023/061895
PCT Pub. Date: Apr. 20, 2023

(65) Prior Publication Data
US 2026/0130649 A1 May 14, 2026

Related U.S. Application Data

(60) Provisional application No. 63/255,036, filed on Oct. 13, 2021.

(51) Int. Cl.
*A61B 8/00* (2006.01)
*A61B 8/06* (2006.01)

(52) U.S. Cl.
CPC ............... *A61B 8/481* (2013.01); *A61B 8/06* (2013.01); *A61B 8/483* (2013.01)

(58) Field of Classification Search
CPC ........... A61B 8/481; A61B 8/06; A61B 8/483
See application file for complete search history.

(56) References Cited

U.S. PATENT DOCUMENTS

2008/0269611 A1  10/2008  Pedrizzetti et al.
2014/0147013 A1  5/2014  Shandas et al.

FOREIGN PATENT DOCUMENTS

WO  2021084060 A1  5/2021

OTHER PUBLICATIONS

International Search Report and Written Opinion for PCT/EP2022/078016; Mailing date: Feb. 6, 2023, 8 pages.
(Continued)

*Primary Examiner* — Michael T Rozanski

(57) ABSTRACT

A method (100) for generating a radial velocity map for a target region, comprising: (i) receiving (120) a series of ultrasound images of the target region; (ii) generating (130) a grid representing the target region and comprising a plurality of points each representing a possible radial center in the target region; (iii) generating (140) a radial flux magnitude map for the grid comprising a radial contrast flux for each of the points, comprising the following which are repeated until a radial contrast flux is calculated for each of the points: selecting (142) one of the points as a radial center; calculating (144) a radial velocity field for a first region around the selected point; and determining (146) a
(Continued)

Flux magnitude map radial contrast flux for the first region; and (iv) automatically selecting (150) a radial center for the series of contrast images.

16 Claims, 6 Drawing Sheets

(56)                    References Cited

OTHER PUBLICATIONS

Christensen-Jeffries, K. et al, "Super-Resolution Ultrasound Imaging," Ultrasound in Medicine & Biology, 2020, vol. 46, Issue 4, pp. 865-891.

Yukhnev, A.D. et al., "Swirling Flow Visualization in Blood Vessels and its Hydrodynamic Models," 15th International Symposium on Flow Visualization, 2012, 10 pages.

Leow, C.H. et al., "Spatio-Temporal Flow and Wall Shear Stress Mapping Based on Incoherent Ensemble-Correlation of Ultrafast Contrast Enhanced Ultrasound Images," Ultrasound in Med. & Biol., 2018, vol. 44, No. 1, pp. 134-152.

Markl, M. et al., "Fast Phase Contrast Cardiac Magnetic Resonance Imaging: Improved Assessment and Analysis of Left Ventricular Wall Motion," Journal of Magnetic Resonance Imaging, 2002, vol. 15, pp. 642-653.

Yoo, J. et al., "Diagnostic Value of High Frame Rate Contrast-enhanced Ultrasonography and Post-processing Contrast Vector Imaging for Evaluation of Focal Liver Lesions: A Feasibility Study," Ultrasound in Med. & Biol., 2020, vol. 46, Issue 9, pp. 2254-2264.

METHODS AND SYSTEMS FOR AUTOMATED CENTER POSITIONING FOR RADIAL VELOCITY MAPPING IN VECTOR CONTRAST IMAGING

CROSS-REFERENCE TO PRIOR APPLICATIONS

This application is the U.S. National Phase application under 35 U.S.C. § 371 of International Application No. PCT/EP2022/078016, filed on Oct. 10, 2022, which claims the benefit of U.S. Provisional Patent Application No. 63/255,036, filed on Oct. 13, 2021. These applications are hereby incorporated by reference herein.

FIELD OF THE DISCLOSURE

The present disclosure is directed generally to methods and systems for generating a radial velocity map in vector contrast imaging.

BACKGROUND

Contrast-enhanced ultrasound (CEUS) is the ultrasound imaging of a tissue of interest after an intravenous injection of a contrast medium comprising microbubbles and/or nanobubbles of gas. CEUS images are acquired as the microbubbles from the contrast medium wash into and out of a lesion or organ over the duration of the contrast bolus. The dynamic wash-in and wash-out patterns exhibited by the lesion or organ of interest are then utilized to characterize the lesion or disease.

Vector contrast imaging (VCI) has recently emerged as an innovative approach to visualize and quantify microbubble movement and velocity as a vector (with both magnitude and direction), with the goal of providing more confident analysis and diagnosis. There are various features available for bubble mapping and visualization with VCI, including velocity magnitude, velocity direction, and radial velocity with respect to a predetermined radial center. For the sake of easy visualization of vascularity, a temporal-accumulation display is often utilized as locations and/or velocities of contrast microbubbles perfusing the lesion or organ on each frame are accumulated over all selected frames.

However, although VCI can provide a map of microbubble velocity and/or direction, this information is challenging to interpret, especially in the context of complex filling patterns with one or multiple flow centers. In such situations, it is meaningful in physics and effective in hemodynamics (i.e., ultrasound contrast kinetics) to represent the velocity vector in the form of radial velocity with respect to a predetermined radial center that is associated to a reginal blood flow source or drain in the selected CEUS imaging sequence. Further, for analysis of VCI, a directional center should be determined before calculating the spatial distribution and temporal accumulation of radial velocities. Choosing the correct directional center can have a significant impact on the interpretation and understanding of VCI and thus on the patient's condition and diagnosis. However, choosing a direction center can be highly subjective and inaccurate.

SUMMARY OF THE DISCLOSURE

Accordingly, there is a continued need for methods and systems that automatically and objectively determine a directional center for vector contrast imaging during contrast-enhanced ultrasound. Various embodiments and implementations herein are directed to a method and system configured to generate a radial velocity map, including automatically determining a directional center, for a vector contrast imaged region during contrast-enhanced ultrasound. The system receives a series of contrast images of a patient's target region visualized using contrast-enhanced ultrasound. The system then generates a grid representing some or all of the target region and comprising a plurality of points each representing a possible radial center in the target region. The system generates a radial flux magnitude map for the grid comprising a radial contrast flux for each of the plurality of points. The map is generated by the following steps, which are repeated until a radial contrast flux is calculated for each of these plurality of points: (i) select one of plurality of points as a radial center: (ii) calculate, for each of the series of contrast images, a radial velocity field for a first region (e.g., a limited circular region with a predetermined radius) around the selected point; and (iii) determine, for a single accumulated image generated from some or all of the series of contrast images, a radial contrast flux for the first region. The system then automatically selects, using the generated radial flux magnitude map, a radial center for the series of contrast images, where the radial center comprises a point of the plurality of points with a maximum radial contrast flux relative to the remainder of the plurality of points. The system then provides a visualization of the selected radial center and/or the generated radial flux magnitude map to a user via a user interface.

Generally, in one aspect, a method for generating a radial velocity map for a target region is provided. The method includes: (i) receiving a series of contrast images of the target region visualized using contrast-enhanced ultrasound: (ii) generating a grid representing some or all of the target region and comprising a plurality of points each representing a possible radial center in the target region: (iii) generating a radial flux magnitude map for the grid comprising a radial contrast flux for each of the plurality of points, comprising the following steps which are repeated until a radial contrast flux is calculated for each of the plurality of points: (1) selecting one of plurality of points as a radial center: (2) calculating, for each of the series of contrast images, a radial velocity field for a first region around the selected point; and (3) determining, for a single accumulated image generated from some or all of the series of contrast images, a radial contrast flux for the first region; and (iv) automatically selecting, using the generated radial flux magnitude map, a radial center for the series of contrast images, wherein the radial center comprises a point of the plurality of points with a maximum radial contrast flux relative to the remainder of the plurality of points.

According to an embodiment, determining radial contrast flux comprises the steps of: determining a radial flux volume by summing, for a single accumulated image generated from some or all of the series of contrast images, the calculated radial velocity field over all pixels within the first region; and dividing the determined radial flux volume by time and by area of the first region.

According to an embodiment, the determining a radial flux volume (RFV) comprises the equation $RFV=\Sigma (V_r \cdot \Delta S \cdot \Delta T)$ where $V_r$=radial velocity field, $\Delta S$=area coverage of one pixel in 2D contrast images, and $\Delta T$=time interval between two consecutive images in the series of contrast images. Note that $\Delta S$=volume of one voxel in the series of 3D contrast images.

According to an embodiment, dividing the determined radial flux volume by time and by area of the first region to generate radial contrast flux (Flux) comprises the equation Flux=RFV/T/A where $T=\Delta T \cdot (N_2-N_1)$ where $N_1$ is a starting image in the series of contrast images and $N_2$ is an ending image in the series of contrast images, and A=area of the first region for 2D contrast images. Note that A=volume of the first region for 3D contrast images.

According to an embodiment, the plurality of points are equidistantly spaced within the grid.

According to an embodiment, the plurality of points comprises fewer than all pixels within the target region.

According to an embodiment, the density of the plurality of points within the grid is automatically determined.

According to an embodiment, the method further includes the step of providing, via a user interface, the selected radial center and/or the generated radial flux magnitude map.

According to a second aspect is a system for generating a radial velocity map for a target region. The system includes a series of contrast images of the target region visualized using contrast-enhanced ultrasound. The system also includes a processor that is configured to: (i) generate a grid representing some or all of the target region and comprising a plurality of points each representing a possible radial center in the target region: (ii) generate a radial flux magnitude map for the grid comprising a radial contrast flux for each of the plurality of points, comprising the following steps which are repeated until a radial contrast flux is calculated for each of the plurality of points: (a) selecting one of plurality of points as a radial center: (b) calculating, for each of the series of contrast images, a radial velocity field for a first region around the selected point; and (c) determining, for a single accumulated image generated from some or all of the series of contrast images, a radial contrast flux for the first region; and (iii) select, using the generated radial flux magnitude map, a radial center for the series of contrast images, wherein the radial center comprises a point of the plurality of points with a maximum radial contrast flux relative to the remainder of the plurality of points. The system also includes a user interface configured to provide the selected radial center.

According to an embodiment, the user interface is further configured to provide the generated radial flux magnitude map.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. The figures showing features and ways of implementing various embodiments and are not to be construed as being limiting to other possible embodiments falling within the scope of the attached claims. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method configured to automatically determining a directional center for a vector contrast imaged region in contrast-enhanced ultrasound. More generally, Applicant has recognized and appreciated that it would be beneficial to provide a method and system to significantly improve the analysis of vector contrast imaging. Accordingly, a radial velocity mapping system receives a series of contrast images of a patient's target region visualized using contrast-enhanced ultrasound. The system then generates a grid representing some or all of the target region and comprising a plurality of points each representing a possible radial center in the target region. The system generates a radial flux magnitude map for the grid comprising a radial contrast flux for each of the plurality of points. The map is generated by the following steps, which are repeated until a radial contrast flux is calculated for each of these plurality of points: (i) select one of plurality of points as a radial center: (ii) calculate, for each of the series of contrast images, a radial velocity field for a first region around the selected point; and (iii) determine, for a single accumulated image generated from some or all of the series of contrast images, a radial contrast flux for the first region. The system then automatically selects, using the generated radial flux magnitude map, a radial center for the series of contrast images, where the radial center comprises a point of the plurality of points with a maximum radial contrast flux relative to the remainder of the plurality of points. The system then provides a visualization of the selected radial center and/or the generated radial flux magnitude map to a user via a user interface.

Thus, according to an embodiment, the methods and systems described or otherwise envisioned herein create quantitative flow parameters for objective documentation of directional flow patterns. The methods and systems identify central locations for outward flow as sources and central locations for inward flow as sinks from quantitative flow parameter maps. Further, the methods and systems enable automatic positioning of direction centers for radial velocity imaging based on sources and/or drains in directional flow patterns.

According to an embodiment, the systems and methods described or otherwise envisioned herein can, in some non-limiting embodiments, be implemented as an element for a commercial product for contrast-enhanced ultrasound methods or systems.

Figure 1:
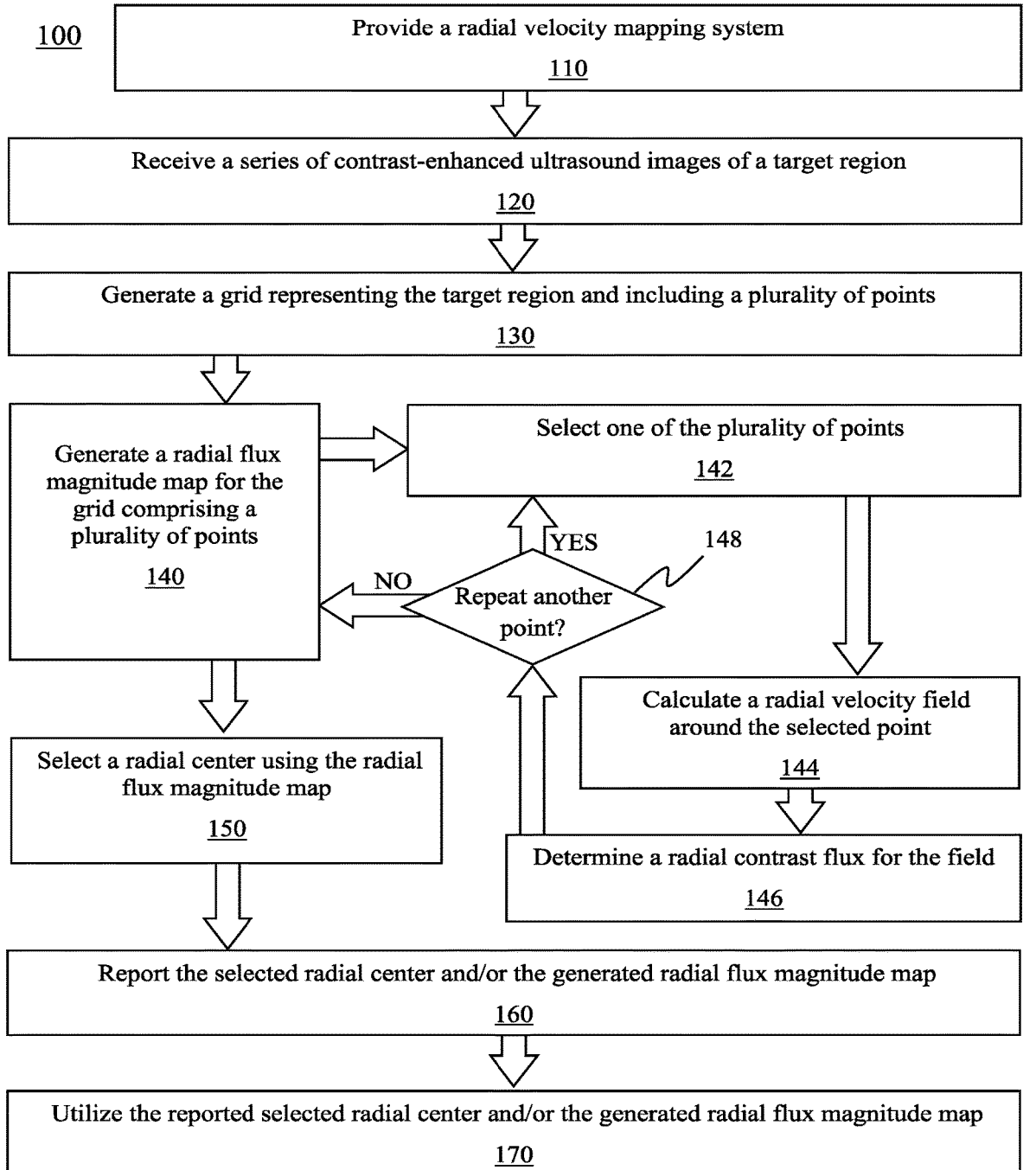
FIG. 1 is a flowchart of a method for generating a radial velocity map, in accordance with an embodiment.

Referring to FIG. 1, in one embodiment is a flowchart of a method 100 for generating a radial velocity map for a target region using a radial velocity mapping system. The methods described in connection with the figures are provided as examples only, and shall be understood not limit the scope of the disclosure. The radial velocity mapping system can be any of the systems described or otherwise envisioned herein. The radial velocity mapping system can be a single system or multiple different systems.

Figure 2:
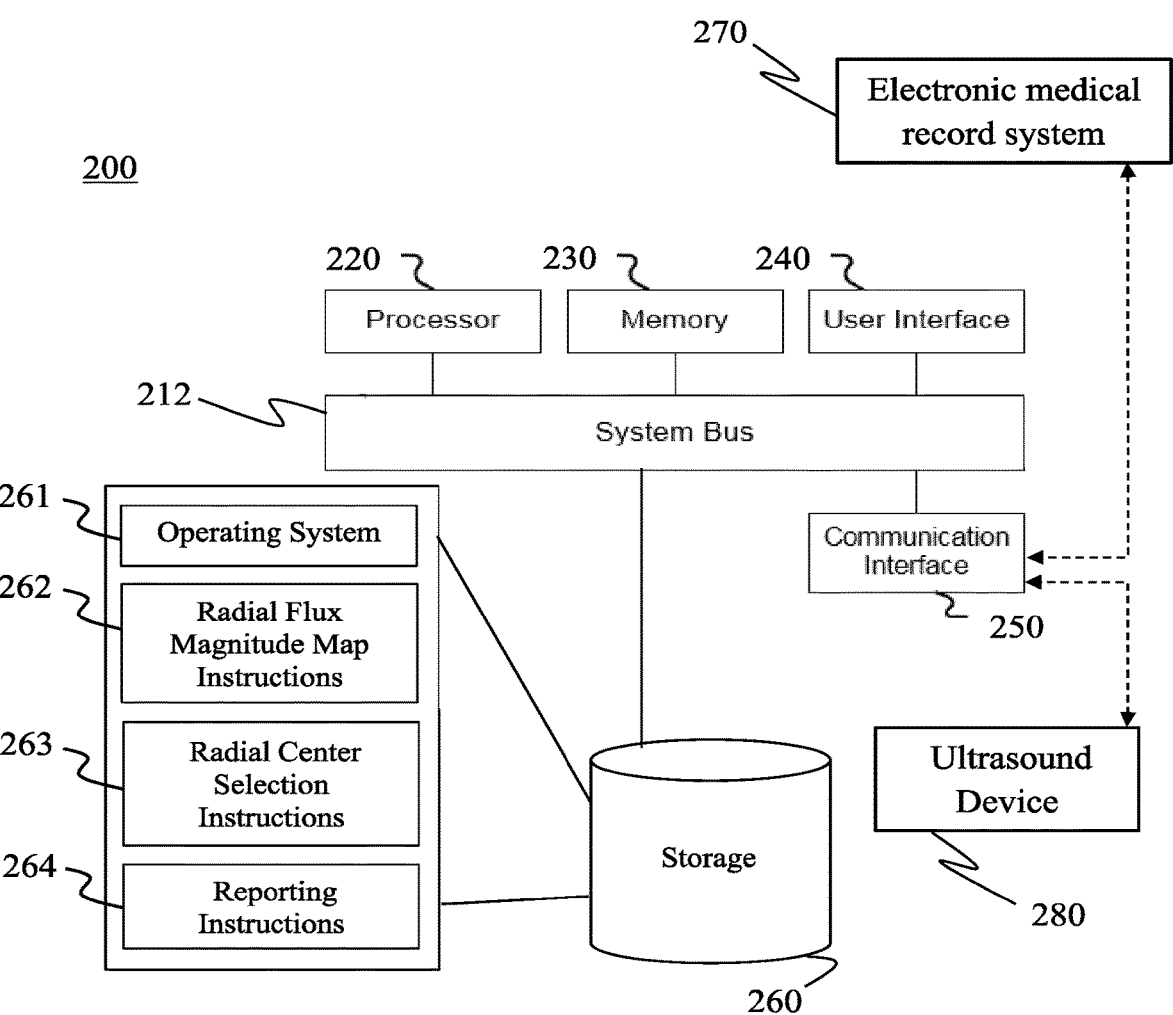
FIG. 2 is a schematic representation of a radial velocity mapping system, in accordance with an embodiment.

At step 110 of the method, a radial velocity mapping system is provided. Referring to an embodiment of a radial velocity mapping system 200 as depicted in FIG. 2, for example, the system comprises one or more of a processor 220, memory 230, user interface 240, communications interface 250), and storage 260, interconnected via one or more system buses 212. It will be understood that FIG. 2 constitutes, in some respects, an abstraction and that the actual organization of the components of the system 200 may be different and more complex than illustrated. Additionally, radial velocity mapping system 200 can be any of the systems described or otherwise envisioned herein. Other elements and components of radial velocity mapping system 200 are disclosed and/or envisioned elsewhere herein.

At step 120 of the method, a series of ultrasound images are received. The ultrasound images can be any images capable of being utilized for this method. According to one embodiment, the series of ultrasound images are obtained over a predetermined period of time via contrast-enhanced ultrasound in which a region of interest in a patient is imaged after introduction of a contrast medium comprising microbubbles and/or nanobubbles of gas. The images are then acquired as the bubbles from the contrast medium move into and out of one or more components of the region of interest, such as a tumor or organ among other possible components. According to an embodiment, the images are such that vector contrast imaging (VCI) can be utilized to visualize and quantify microbubble direction and velocity. There are various features available for bubble mapping and visualization with VCI, including velocity magnitude, velocity direction, and radial velocity with respect to a predetermined radial center.

According to an embodiment, the ultrasound device utilized to obtain the contrast-enhanced ultrasound images is a component of the radial velocity mapping system. However, according to another embodiment, the ultrasound device utilized to obtain the contrast-enhanced ultrasound images is not a component of the radial velocity mapping system, and instead the system receives the images from a local or remote ultrasound system. A local or remote ultrasound system-which may or may not be a component of the radial velocity mapping system-obtains the images for immediate or future analysis. Thus, the contrast-enhanced ultrasound images may be utilized, before or after any image processing, immediately or may be stored in local or remote storage for use in further steps of the method. For immediate analysis, the system may receive or otherwise obtain the images from the ultrasound device. For subsequent analysis, the system may receive or otherwise obtain the images from storage.

At step 130 of the method, the radial velocity mapping system generates a grid that represents some or all of the visualized target region, and that comprises a plurality of points within or otherwise in or on the grid. Each of these points are a possible radial center for the gridded target region. To perform vector contrast imaging (VCI) for a target region with one or multiple blood flow sources and/or drains, the direction and velocity of bubble movement is quantified or visualized with regard to a radial center. A radial center can be determined or predetermined manually, although this introduces subjectivity in the VCI analysis. Using the methods and systems described or otherwise envisioned herein, the radial velocity mapping system provides an objective method for determining the radial center. According to an embodiment, the grid is generated in memory of the system. The plurality of points may be automatically determined by the system, and the points may be randomly spaced or can be equidistantly spaced relative to each other within the grid.

At step 140 of the method, the radial velocity mapping system generates a radial flux magnitude map for the generated grid. The radial flux magnitude map includes a radial contrast flux for some or all of the plurality of points in the grid. The radial flux magnitude map facilitates selection by the system of a radial center. The radial flux magnitude map can be generated using a variety of mechanisms, including the methods described or otherwise envisioned herein.

According to an embodiment, the following method is utilized to generate the radial flux magnitude map, although the example is non-limiting. The method is repeated until each of the plurality points, or all of the plurality of points intended to be utilized, comprise a calculated radial contrast flux.

At step 142, one of the plurality of points is selected as a radial center. This can be based on random selection, or based on some input either from a user or from the system. For example, a user may designate a temporary or permanent point in a grid to be the first radial center. As another example, the system may select a first point as a first radial center based by selecting the same point every time, or by randomly selecting a point. The next point selected as the second radial center can be based on the selection of the first point, or can be similarly random or user-selected.

At step 144, the system calculates a radial velocity field for a first region around the selected point, for a plurality of the series of obtained or received contrast images. According to an embodiment, the system can select a sequence of the obtained or received contrast images, comprising some or all of the images, beginning with starting image or frame Ny and terminating with ending image or frame $N_n$.

According to an embodiment, the region around the first selected point for which the radial velocity field is calculated can be any shape or size. The shape and/or size of the region can be based on the generated grid, selected point, target region, predetermined or preprogrammed parameters, and/or on any other element. According to an embodiment, the region is a circular area with a first diameter and having the first selected point at the center of the circle.

Figure 3:
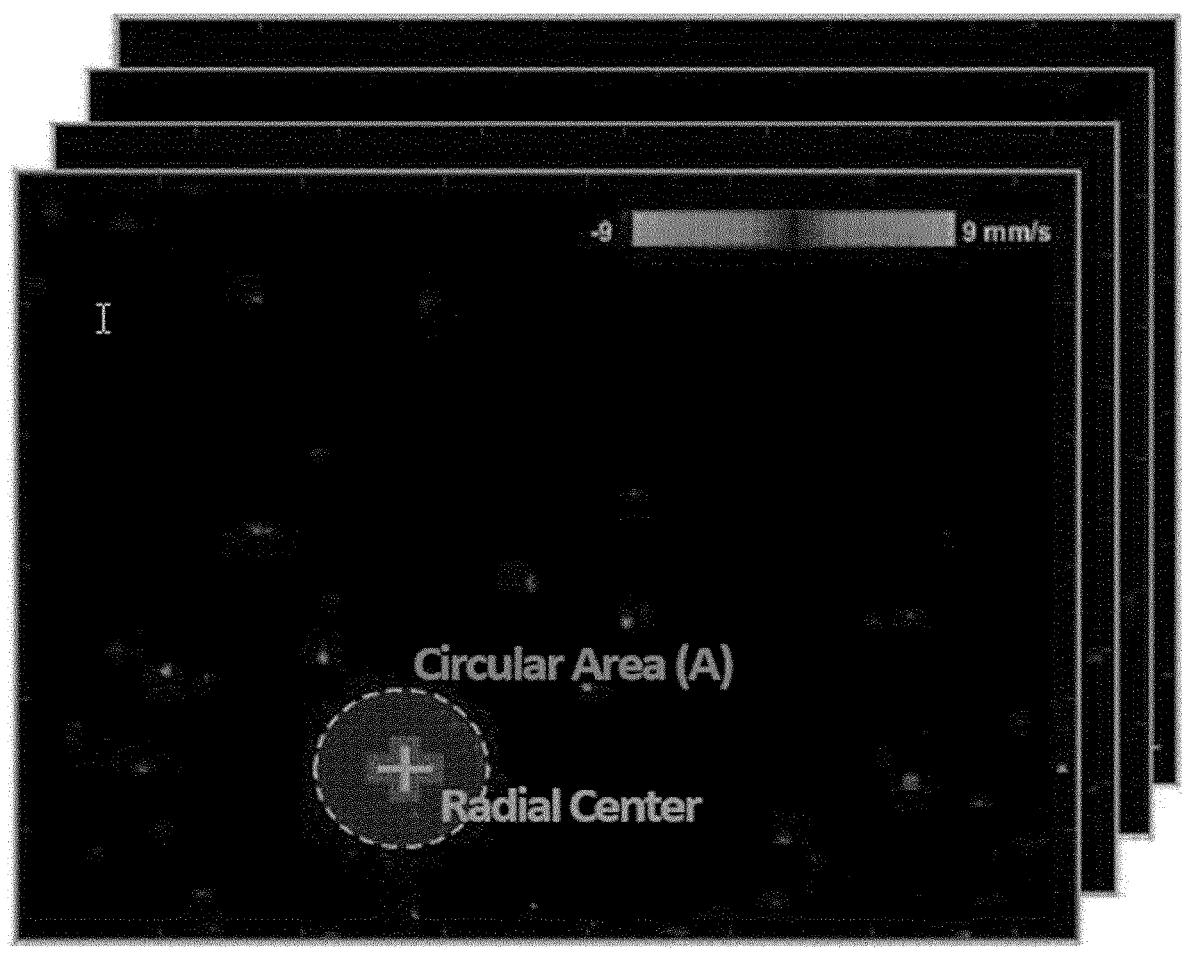
FIG. 3 is a schematic representation of a series of contrast-enhanced ultrasound images each comprising a selected first point ("Radial Center") and a selected first region ("Circular Area") surrounding the selected first point, in accordance with an embodiment.

Referring to FIG. 3, in one embodiment, is a series of contrast-enhanced ultrasound images each comprising the selected first point ("Radial Center") and a selected first region ("Circular Area") surrounding the selected first point. Although shown as a circle in the figure, the first region can be any shape and size.

The system determines a radial velocity field $V_R$ around the radial center for each of the selected frames ($N_1 \ldots N_n$). The radial velocity field $V_R$ can be calculated using any method or mechanism for determining a radial velocity field. According to an embodiment, the radial velocity field is calculated using an image cross-correlation method for image pixel displacements (i.e., block matching) or the Hungarian algorithm for microbubble pairing and tracking, although other methods are possible. According to an embodiment, the Hungarian algorithm is more accurate when tracking microbubbles across multiple frames, but less efficient in computational cost than the image cross-correlation based method. Other methods are possible. The calculated radial velocity field $V_R$ can be utilized immediately or stored in local or remote memory for subsequent us.

At step 146, the system determines, for a single accumulated image generated from some or all of the series of contrast images, a radial contrast flux for the first region around the selected point. The radial contrast flux can be determined according to a wide variety of methods.

According to one embodiment for determining the radial contrast flux, the system sums, for a single accumulated image generated from some or all of the series of contrast images ($N_1 \ldots N_n$), the calculated radial velocity field over all pixels within the selected first region, and divides the determined radial flux volume by time and by area of the selected first region. For example, determining the radial flux volume (RFV) enclosed within the selected first region can comprise the equation:

$$RFV = \sum (V_r \cdot \Delta S \cdot \Delta T) \qquad \text{(Eq. 1)}$$

where $V_r$=radial velocity field, $\Delta S$=area coverage of one pixel for 2D images or volume coverage of one voxel for 3D images, and $\Delta T$=time interval between two consecutive images in the series of contrast images ($N_1 \ldots N_n$).

According to an embodiment, dividing the determined radial flux volume by time and by area of the first region to generate radial contrast flux (Flux) comprises the equation:

$$\text{Flux} = RFV/T/A \qquad \text{(Eq. 2)}$$

where $T=\Delta T \cdot (N_n - N_1)$ where $N_1$ is the starting image in the series of contrast images and $N_n$ is the ending image in the series of contrast images, and A=area of the first region for 2D images or volume of the first region for 3D images.

Steps 142, 144, and 146 are repeated for each of the plurality of points in the generated grid, after which this method loop concludes at step 140. For example, at decision point 148 in FIG. 1, the system asks whether steps 142, 144, and 146 will be repeated for an additional one of the plurality of points. If yes, then the system proceeds to step 142. If no, then the system proceeds to step 140. Notably, however, this is just one example of a method for determining the radial contrast flux. At the conclusion of step 140, however, the system comprises a radial flux magnitude map for the generated grid. The generated radial flux magnitude map may be utilized immediately, or may be saved in local or remote storage for subsequent use by the method.

At step 150 of the method, the radial velocity mapping system utilizes the generated radial flux magnitude map to objectively choose a radial center. According to an embodiment, the radial velocity mapping system automatically selects the radial center using the generated radial flux magnitude map. For example, the system can select the point within the plurality of points that comprises a maximum radial contrast flux relative to the remainder of the plurality of points.

Figure 4A:
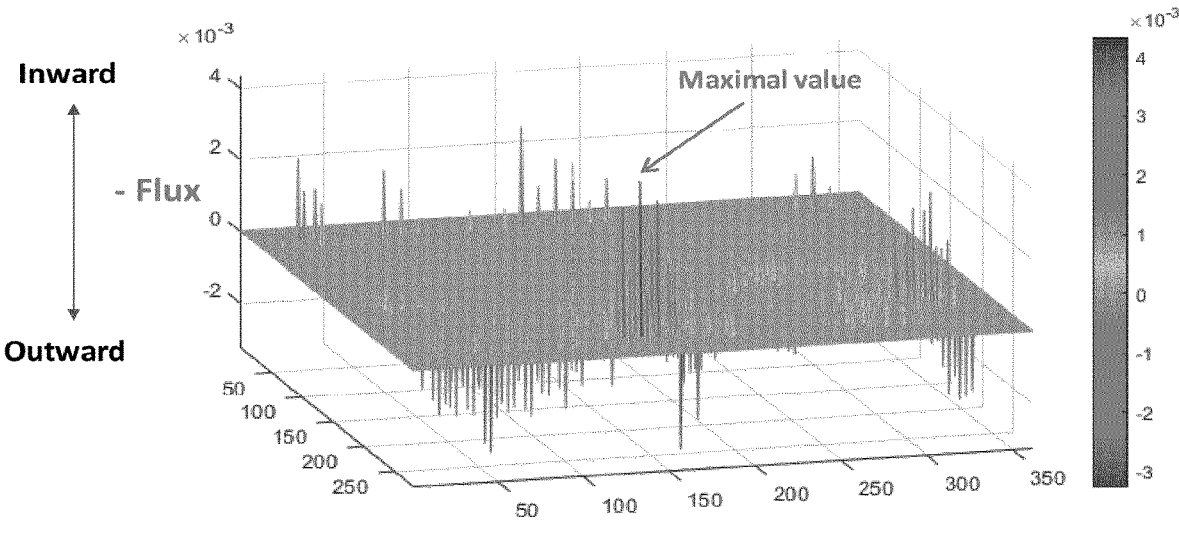
FIG. 4A is a radial flux map showing original values, in accordance with an embodiment.
Figure 4B:
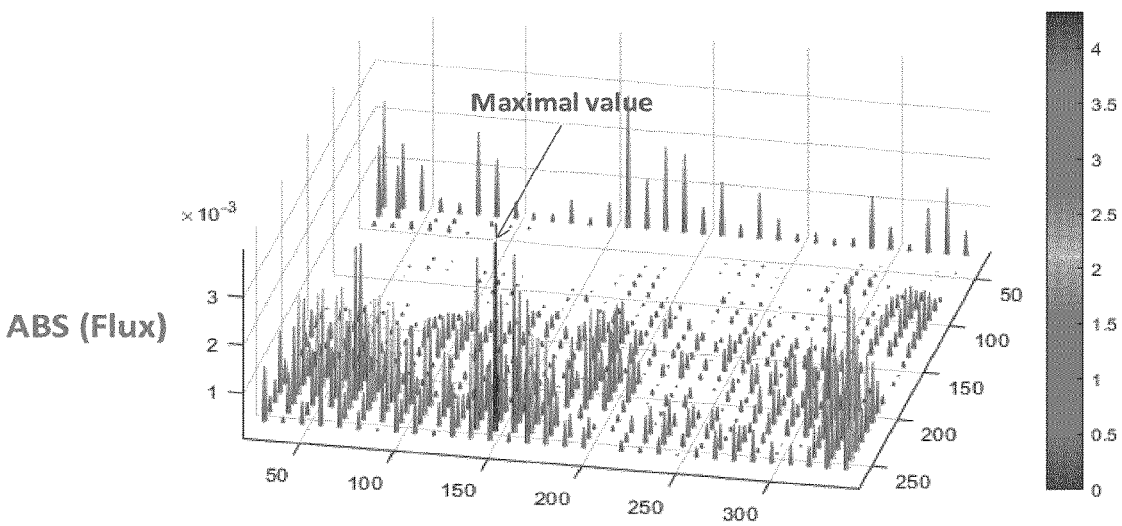
FIG. 4B is a radial flux map showing absolute values of radial flux, in accordance with an embodiment.

Referring to FIGS. 4A and 4B, for example, are examples of a radial flux magnitude map for 2D contrast images, generated using the image cross-correlation method, that can be utilized to select the radial center. FIG. 4A is a radial flux map showing original values (thus with positive and negative flux), while FIG. 4B is a radial flux map showing absolute values of radial flux (mL/s/cm²). For this non-limiting example, the maps were constructed over a 2D grid spaced every 10 pixels (0.8 mm) in both dimensions of a ROI within contrast images for a human abnormal thyroid. The original and absolute values of radial flux were calculated across 200 frames (after initial contrast appearance) over a circular area with a radius of 25 pixels (2 mm). Other parameters are possible.

According to an embodiment, spatial distribution maps of flow parameters (such as the radial contrast flux and its magnitude in FIGS. 4A and 4B) can be constructed for quantifying directional flow patterns. For the radial flux calculation, it may be important to select an adequate diameter of the radial area (as the selected first region) for maintaining both low variations in the flux computation (lower with a larger circle area) and sensitive spatial distributions (higher with a smaller circle area). It may also be important to properly select the timing and length of the images sequence. These parameters may be predetermined or experimentally derived.

Figure 5:
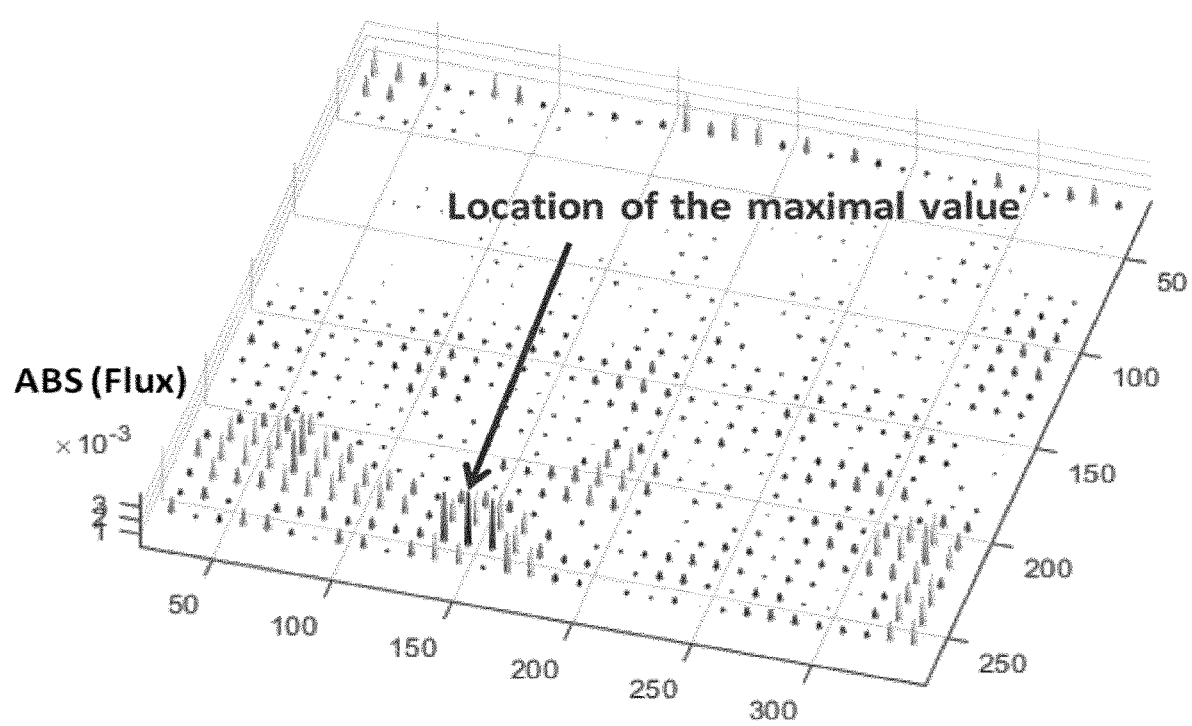
FIG. 5 is a radial flux magnitude map indicating a location for a maximal flux value in both inward and outward radial directions, in accordance with an embodiment.
Figure 6:
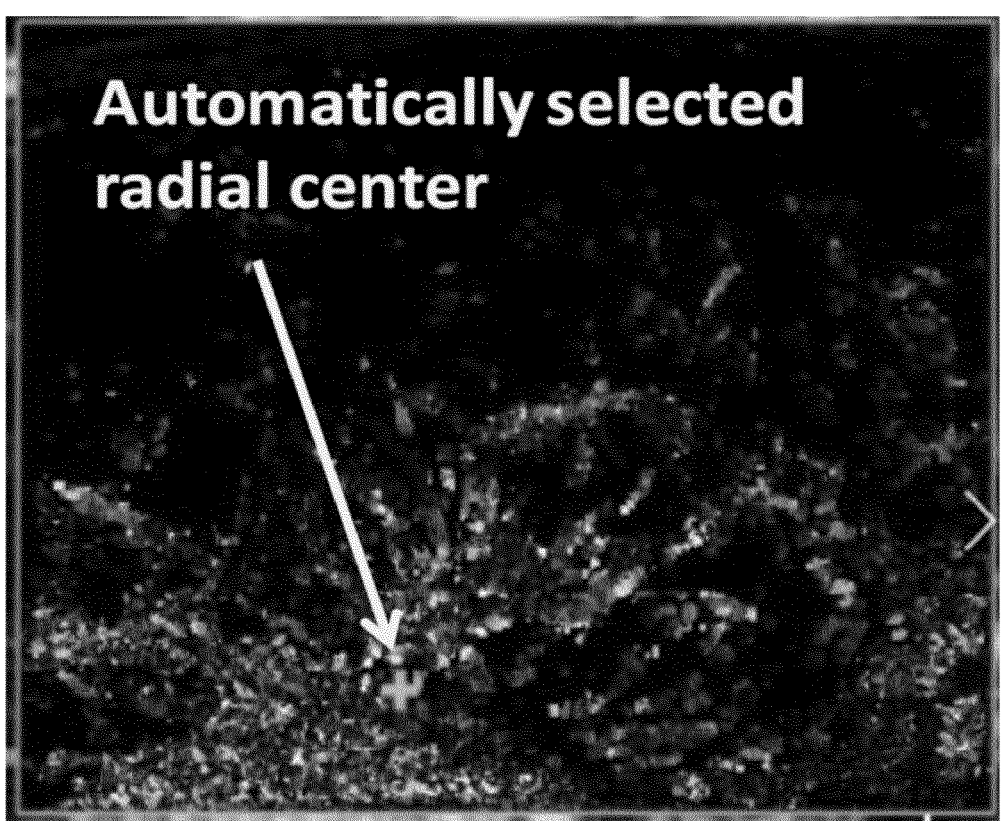
FIG. 6 is a radial flow velocity map with its radial center automatically determined by the location of the maximal flux value in the radial flux magnitude map, in accordance with an embodiment.

According to an embodiment, the radial center in the radial velocity map represents a focal point in a complex flow pattern, so spatial distribution maps of quantitative flow parameters can be utilized for automatic selection of the radial center. As demonstrated in FIGS. 5 and 6 for two-dimensional (2D) VCI based on the image cross-correlation method, the location for the maximal flux magnitude value in the radial flux magnitude map (FIG. 5) can be used directly as the radial center for a radial flow velocity map (FIG. 6). This is an example for an automatic selection of the radial center using a quantitative flow map. Thus, FIG. 5 comprises a radial flux magnitude map indicating the location for the maximal flux value in both inward and outward radial directions. FIG. 6 comprises a radial flow velocity map with its radial center automatically determined by the location of the maximal flux value in the radial flux magnitude map.

According to one non-limiting embodiment, a user can select a grid size and/or area per grid point, and the system will automatically calculate the map and automatically locate the highest influx/efflux point(s) and display the values. A threshold could be set to limit the algorithm to only the highest points and therefore the maximum absolute values. According to an embodiment, the flux can be tied to the divergence theorem (Gauss law). Therefore, the system may alternatively calculate the divergence of the velocity vector field and use this to compute the flux directly.

According to an embodiment, radial flux can also be separated into 'outward flux' only for centrifugal flow (moving in a direction away from a center or axis) and 'inward flux' only for centripetal flow (moving in a direction toward a center or axis). Outward flux can be calculated with only the positive radial velocity ($V_R>0$)) while inward flux can be computed with only the negative radial velocity ($V_R<0$)). The radial flux can thus be a summation of outward and inward radial fluxes. According to an embodiment, inward and outward radial fluxes can be especially useful for Hungarian algorithm-based VCI maps. This is because opposite flows closely next to each other can be imaged separately via tracking of individual microbubbles over multiple frames on such VCI maps. The radial centers in inward, outward, and regular radial velocity maps can be determined from, respectively, the locations for the maximal absolute values in the inward flux map (only with $V_R<0$)), the outward flux map (only with $V_R > 0$) and the regular flux map (i.e., inward-and-outward flux summation map). Many other methods are possible.

At step 160 of the method, the system provides a report comprising one or more of the selected radial center and the generated radial flux magnitude map, among other possible information. The system can provide the report to a clinician or other user via a user interface of the system. The display may also comprise information about the patient, the contrast-enhanced ultrasound, and/or any other information. Any of the information may be communicated by wired and/or wireless communication to another device. For example, the system may communicate the information to a mobile phone, computer, laptop, wearable device, and/or any other device configured to allow display and/or other communication of the report. The user interface can be any device or system that allows information to be conveyed and/or received, and may include a display, a mouse, and/or a keyboard for receiving user commands.

At optional step 170 of the method, the information generated by step 160 is electronically provided by the system to a clinician or other decisionmaker who then utilizes the displayed graphics with the selected radial center and/or the generated radial flux magnitude map for patient care decision-making. For example, the clinician or other decisionmaker can utilize the displayed graphics, such as a radial flow velocity map with the automatically selected radial center, to interpret blood flow at a lesion, organ, tumor, or other target area. Interpretation of blood flow is a diagnosis, for example, and thus this diagnosis can be utilized to select a treatment or other care option for the patient. Many other implementations are possible, such as providing the information automatically into a Clinical Decision Support (CDS) system for subsequent us.

Referring to FIG. 2 is a schematic representation of a radial velocity mapping system 200. System 200 may be any of the systems described or otherwise envisioned herein, and may comprise any of the components described or otherwise envisioned herein. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. For example, a computer-readable storage medium embodied in non-transitory memory may comprise instructions which, when executed by a computer or the processor 220, cause the computer or processor to carry out the steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, the electronic medical record system 270 is an electronic medical records database from which the information about the patient, including ultrasound images obtained from/for the patient, may be obtained or received. The electronic medical records database may be a local or remote database and is in direct and/or indirect communication with the radial velocity mapping system 200. Thus, according to an embodiment, the radial velocity mapping system comprises an electronic medical record database or system 270.

According to an embodiment, the system comprises an ultrasound device 280. The ultrasound device may be any ultrasound capable of capturing the contrast-enhanced images as described or otherwise envisioned herein. According to another embodiment, rather than comprising an ultrasound device, the system may simply be in wireless and/or wired communication with a local or remote ultrasound device from which one or more ultrasound images are obtained or otherwise received.

According to an embodiment, storage 260 of system 200 may store one or more algorithms, modules, and/or instructions to carry out one or more functions or steps of the methods described or otherwise envisioned herein. For example, the system may comprise, among other instructions or data, radial flux magnitude map instructions 262, radial center selection instructions 263, and/or reporting instructions 264.

According to an embodiment, radial flux magnitude map instructions 262 direct the system to generate the radial flux magnitude map. According to an embodiment, the radial flux magnitude map includes a radial contrast flux for some or all of the plurality of points in the grid. The radial flux magnitude map can be generated using a variety of mechanisms. According to an embodiment, the system selects one of the plurality of points in a grid as a radial center. The system then calculates a radial velocity field for a first region around the selected point, for a plurality of the series of obtained or received contrast images. The system then determines, for a single accumulated image generated from some or all of the series of contrast images, a radial contrast flux for the first region around the selected point.

According to an embodiment, radial center selection instructions 263 direct the system to automatically select a radial center using a generated radial flux magnitude map. According to an embodiment, the system can select the point within the plurality of points that comprises a maximum radial contrast flux relative to the remainder of the plurality of points. Other methods are possible.

According to an embodiment, reporting instructions 264 direct the system to generate and provide to a user via a user interface information comprising one or more of the selected radial center, the generated radial flux magnitude map, and a radial flow velocity map with the automatically selected radial center. The display may also comprise information about the patient, the contrast-enhanced ultrasound, and/or any other information. Any of the information may be communicated by wired and/or wireless communication to another device. For example, the system may communicate the information to a mobile phone, computer, laptop, wearable device, and/or any other device configured to allow display and/or other communication of the report. The user interface can be any device or system that allows information to be conveyed and/or received, and may include a display, a mouse, and/or a keyboard for receiving user commands.

According to an embodiment, the radial velocity mapping system is configured to process many thousands or millions of datapoints to generate a radial flow velocity map with an automatically selected radial center. For example, generating a radial flux magnitude map for the plurality of points in the generated grid for the images comprises millions or billions of calculations. Each generated radial flux magnitude map is a novel map that has never before existed, and comprises millions of datapoints and millions or billions of calculations. Automatically selecting the radial center, and then generating and displaying the radial flow velocity map with the automatically selected radial center further comprises millions more calculations. Thus, generating and providing a radial flow velocity map with an automatically selected radial center comprises a process with a volume of calculation and analysis that a human brain cannot accomplish in a lifetime, or multiple lifetimes. By providing an improved analysis of contrast-enhanced ultrasound imagery, the novel radial velocity mapping system and method has an enormous positive impact and effect on ultrasound imagery and analysis compared to prior art systems.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or." as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of." or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "cither," "one of." "only one of." or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising." "including." "carrying." "having." "containing." "involving." "holding." "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for generating a radial velocity map for a target region, comprising:
    receiving a series of contrast images of the target region visualized using contrast-enhanced ultrasound;
    generating a grid representing some or all of the target region and comprising a plurality of points each representing a possible radial center in the target region;
    generating a radial flux magnitude map for the grid comprising a radial contrast flux for each of the plurality of points, comprising the following steps which are repeated until a radial contrast flux is calculated for each of the plurality of points:
    selecting one of plurality of points as a radial center;
    calculating, for each of the series of contrast images, a radial velocity field for a first region around the selected point; and
    determining, for a single accumulated image generated from some or all of the series of contrast images, a radial contrast flux for the first region; and
    automatically selecting, using the generated radial flux magnitude map, a radial center for the series of contrast images, wherein the selected radial center comprises a point of the plurality of points with a maximum radial contrast flux relative to the remainder of the plurality of points.

2. The method of claim 1, wherein determining radial contrast flux comprises the steps of:
    determining a radial flux volume by summing, for a single accumulated image generated from some or all of the series of contrast images, the calculated radial velocity field over all pixels within the first region; and
    dividing the determined radial flux volume by time and by area of the first region.

3. The method of claim 2, wherein determining a radial flux volume (RFV) comprises the equation:

$$RFV = \sum (V_r \cdot \Delta S \cdot \Delta T)$$

where $V_r$=radial velocity field, $\Delta S$=area coverage of one pixel for 2D images or volume coverage of one voxel for 3D images, and $\Delta T$=time interval between two consecutive images in the series of contrast images.

4. The method of claim 2, wherein dividing the determined radial flux volume by time and by area of the first region to generate radial contrast flux (Flux) comprises the equation:

$$Flux = RFV/T/A$$

where $T=\Delta T \cdot (N_2 - N_1)$ where $N_1$ is a starting image in the series of contrast images and $N_2$ is an ending image in the series of contrast images, and A=area of the first region for 2D images or volume of the first region for 3D images.

5. The method of claim 1, wherein the plurality of points are equidistantly spaced within the grid.

6. The method of claim 1, wherein the plurality of points comprises fewer than all pixels within the target region.

7. The method of claim 1, wherein a density of the plurality of points within the grid is automatically determined.

8. The method of claim 1, further comprising the step of providing, via a user interface, the selected radial center and/or the generated radial flux magnitude map.

9. A computer-readable storage medium embodied in non-transitory memory comprising instructions which, when executed by a computer, cause the computer to carry out the steps of the method of claim 1.

10. A system for generating a radial velocity map for a target region, comprising:
    a series of contrast images of the target region visualized using contrast-enhanced ultrasound;
    a processor configured to: (i) generate a grid representing some or all of the target region and comprising a plurality of points each representing a possible radial center in the target region; (ii) generate a radial flux magnitude map for the grid comprising a radial contrast flux for each of the plurality of points, comprising the following steps which are repeated until a radial contrast flux is calculated for each of the plurality of points: (a) selecting one of plurality of points as a radial center; (b) calculating, for each of the series of contrast images, a radial velocity field for a first region around the selected point; and (c) determining, for a single accumulated image generated from some or all of the series of contrast images, a radial contrast flux for the first region; and (iii) select, using the generated radial flux magnitude map, a radial center for the series of contrast images, wherein the selected radial center comprises a point of the plurality of points with a maximum radial contrast flux relative to the remainder of the plurality of points; and
    a user interface configured to provide the selected radial center.

11. The system of claim 10, wherein determining radial contrast flux comprises the steps of:

determining a radial flux volume by summing, for a single accumulated image generated from some or all of the series of contrast images, the calculated radial velocity field over all pixels within the first region; and dividing the determined radial flux volume by time and by area of the first region.

12. The system of claim 11, wherein determining a radial flux volume (RFV) comprises the equation:

$$RFV = \sum (V_r \cdot \Delta S \cdot \Delta T)$$

where $V_r$=radial velocity field, $\Delta S$=area coverage of one pixel for 2D images or volumetric coverage of one voxel for 3D images, and $\Delta T$=time interval between two consecutive images in the series of contrast images.

13. The system of claim 11, wherein dividing the determined radial flux volume by time and by area of the first region to generate radial contrast flux (Flux) comprises the equation:

$$Flux = RFV/T/A$$

where $T=\Delta T \cdot (N_2 - N_1)$ where $N_1$ is a starting image in the series of contrast images and $N_2$ is an ending image in the series of contrast images, and A=area of the first region for 2D images or volume of the first region for 3D images.

14. The system of claim 10, wherein the plurality of points are equidistantly spaced within the grid.

15. The system of claim 10, wherein the plurality of points comprises fewer than all pixels within the target region.

16. The system of claim 10, wherein the user interface is further configured to provide the generated radial flux magnitude map.

* * * * *